United States Patent [19]

Yazaki et al.

[11] Patent Number: 4,943,427

[45] Date of Patent: * Jul. 24, 1990

[54] DIAGNOSTIC AGENT FOR HEART DISEASE AND USE THEREOF

[75] Inventors: Yoshio Yazaki, Tokyo; Masahito Sugi, Choshi, both of Japan

[73] Assignee: Yamasa Shoyu Kabushiki Kaisha, Chiba, Japan

[ * ] Notice: The portion of the term of this patent subsequent to Aug. 30, 2005 has been disclaimed.

[21] Appl. No.: 715,815

[22] Filed: Mar. 25, 1985

[30] Foreign Application Priority Data

Mar. 27, 1984 [JP] Japan .................................. 59-58767

[51] Int. Cl.$^5$ .................. A61K 43/00; A61K 39/395; A61K 49/02; G01N 33/53

[52] U.S. Cl. ...................................... 424/1.1; 530/387; 436/548; 935/95; 935/96; 935/99; 935/100; 935/104; 935/107

[58] Field of Search ...................... 424/1.1, 9; 435/68, 435/240.27; 935/99, 100, 102, 104, 106, 107; 436/548

[56] References Cited

U.S. PATENT DOCUMENTS

| | | | |
|---|---|---|---|
| 4,036,945 | 7/1977 | Haber | 424/9 |
| 4,331,647 | 5/1982 | Goldenberg | 424/9 |
| 4,421,735 | 12/1983 | Haber et al. | 424/9 |
| 4,767,843 | 8/1988 | Yazaki et al. | 530/387 |

FOREIGN PATENT DOCUMENTS

131834 1/1985 European Pat. Off. ............. 424/1.1

OTHER PUBLICATIONS

Tsuchimochi et al, J. Clin. Invest., vol. 74, Aug. 1984, pp. 662–665.
Clark et al, Biochem. Biophys. Res. Comm., vol. 95, pp. 1680–1686, Aug. 1980.
Khaw et al, Hybridoma, vol. 3, pp. 11–23, 1984.
Kavirsky et al, J. Biol. Chem., vol. 259, pp. 2775–2781, Mar. 10, 1984.
Tsuchimochi et al, J. Clin. Invest., vol. 74, pp. 662–665, Aug. 1984.
Sinha et al, Proc. Natl. Acad. Sci. USA, vol. 79, pp. 5847–5851, Oct. 1982.
Friedman et al, Proc. Natl. Acad. Sci. USA, vol. 81, pp. 3044–3048, May 1984.
Mahdavi et al., Proc. Natl. Acad. Sci. USA, vol. 81, pp. 2626–2630, May 1984.

*Primary Examiner*—John F. Terapane
*Assistant Examiner*—J. E. Thomas
*Attorney, Agent, or Firm*—Wenderoth, Lind & Ponack

[57] ABSTRACT

A diagnostic agent for heart disease comprising a radiolabeled monoclonal antibody having specificity to cardiac myosin heavy chain or its active fragment is disclosed. The diagnostic agent is useful for topographic diagnosis of heart disease such as myocardial infarction and myocardial disease by imaging.

8 Claims, 3 Drawing Sheets

DIAGNOSTIC AGENT FOR HEART DISEASE AND USE THEREOF

BACKGROUND OF THE INVENTION

1. Field of the Art

The present invention relates to a diagnostic agent useful for diagnosis of heart disease such as myocardial infarction and myocardial disease by imaging, and a method for the diagnosis of heart disease with use of the diagnostic agent.

In recent years, in the diagnosis of heart disease such as myocardial infarction, diagnosis by imaging which involves administering a radiolabeled tracers into a body, detecting γ-rays emitted by the radioisotope to convert the same into an image, processing the image with a computer to obtain a two- or three-dimensional image, and diagnosing the site or size of the myocardial infarction on the basis of the image thus obtained has made rapid progress. However, tracers used heretofore in the diagnosis by imaging in cardiac nuclear medicine have not always been able to depict specifically the site of myocardial infarction.

For example, Tl scintigraphy of myocardium using thallium-201 ($^{201}$Tl) applies the mechanism wherein the Tl behaves in vivo similarly as potassium ion and is taken into cells of the heart liver, kidneys, endocrine organs, tumors and the like where turnover rate is relatively fast, whereby normal cardiac muscle is depicted while the Tl is not ingested into necrotized or ischemic cardiac muscle at an infarction site, which site is depicted as a defect. Accordingly, the Tl does not always depict cardiac muscle specifically, and it has also been difficult to determine by this method whether the infarction occurred recently or in the past.

Pyrophosphate scintigraphy of myocardium, on the other hand, utilizes the phenomenon of technetium —99m($^{99m}$Tc)-labeled pyrophosphate accumulating at an infraction site, which site is depicted as a positive scintigram. This tracer, however, deposits also in the peripheral region of the infarction site and thus is liable to overestimate the infarction area.

2. Prior Art

As a method intended to overcome the above described problems accompanying the conventional tracers, a method using a radiolabeled antibody for cardiac myosin has recently attracted considerable attention. In this method use is made of an antibody obtained by purifying anti-serum prepared by immunizing animals with purified cardiac myosin or its active fragment such as (Fab')$_2$ fragment obtained by treating the antibody with pepsine, both the antibody and its active fragment being radiolabeled and reported to accumulate densely at an infarction site. (cf. U.S. Pat. No. 4,036,945)

However, a myosin molecule has a sub-unit structure comprising two heavy chains and four light chains (two species in the case of human cardiac muscle), so that the anti-serum obtained by immunization with the myosin, even if purified by means of affinity chromatography, also contains antibody molecules specific for light chains. In myocardial infarction, myocardial cell membranes in a necrotized region are destroyed whereby cardiac myosin light chains are released into the blood together with polypeptides such as creatine phosphokinase (CPK) and lactate dehydrogenase. Thus, the antibody having specificity to myosin light chain and its active fragment form an immune complex with the light chain released into the blood and are consumed on the route to the infarction site. Meanwhile, there is the possibility of the immune complex inducing an allergic reaction and various other biological reactions. A further problem is that the anti-serum can be prepared only in a limited quantity and therefore cannot be supplied in a large quantity for clinical purposes.

SUMMARY OF THE INVENTION

We have carried out considerable research with a view to developing tracers which will be accumulated specifically in a myocardial infarction site, ensuring exact diagnosis by imaging. As a result we have conceived and developed this invention.

More particularly, the present invention provides a diagnostic agent comprising a radiolabeled monoclonal antibody having specificity to human cardiac myosin heavy chain or its active fragment and useful for diagnosis of heart disease such as myocardial infarction, myocardial disease and the like.

The present invention, in one aspect thereof, further provides a diagnostic agent for heart disease comprising a radiolabeled monoclonal antibody having specificity to an isozyme of human cardiac myosin heavy chain or its active fragment. As the monoclonal antibody for use in this case, a monoclonal antibody having specificity to human cardiac myosin heavy chain α type or β type is employed.

The present invention, in another aspect thereof, provides a method for the diagnosis of heart disease with use of the diagnostic agent.

BRIEF DESCRIPTION OF THE REFERENCE ILLUSTRATIONS

In the illustrations:

FIG. 1 is a photograph wherein FIGS. 1A, 1B, and 1C are planar images which are respectively an anterior view, a left anterior oblique view, and a side view of the infarction site in the canine ventricular muscle obtained in Practice Example by the use of $^{131}$I-monoclonal antibody (HMC-48);

FIG. 2 is a photograph wherein FIGS. 2A, 2B, 2C, and 2D are single photon emission computed tomography of the infarction site in the canine ventricular muscle obtained in Practice Example by the use of $^{131}$I-monoclonal antibody (HMC-48); and FIG. 3 is a photograph showing the radiolabeled anti-myosin heavy chain monoclonal antibody fragment accumulating at the myocardial infarction site in Experimental Example.

DETAILED DESCRIPTION OF THE INVENTION

Figure 1:
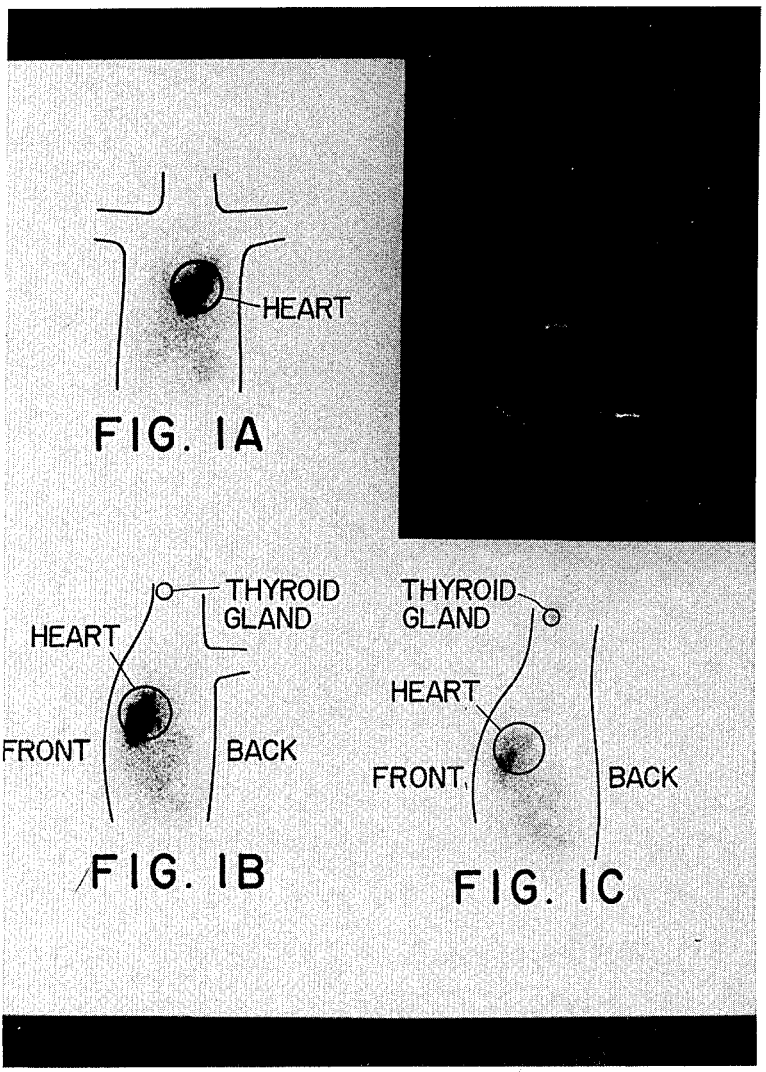
Figure 2:
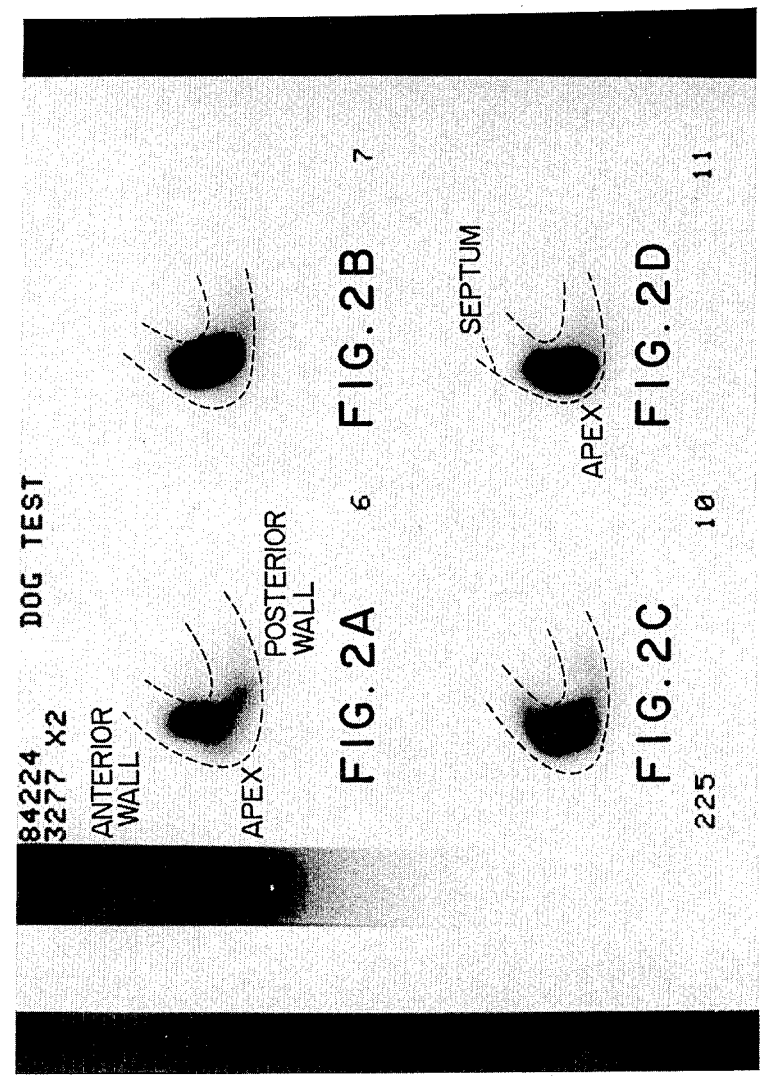
Figure 3:
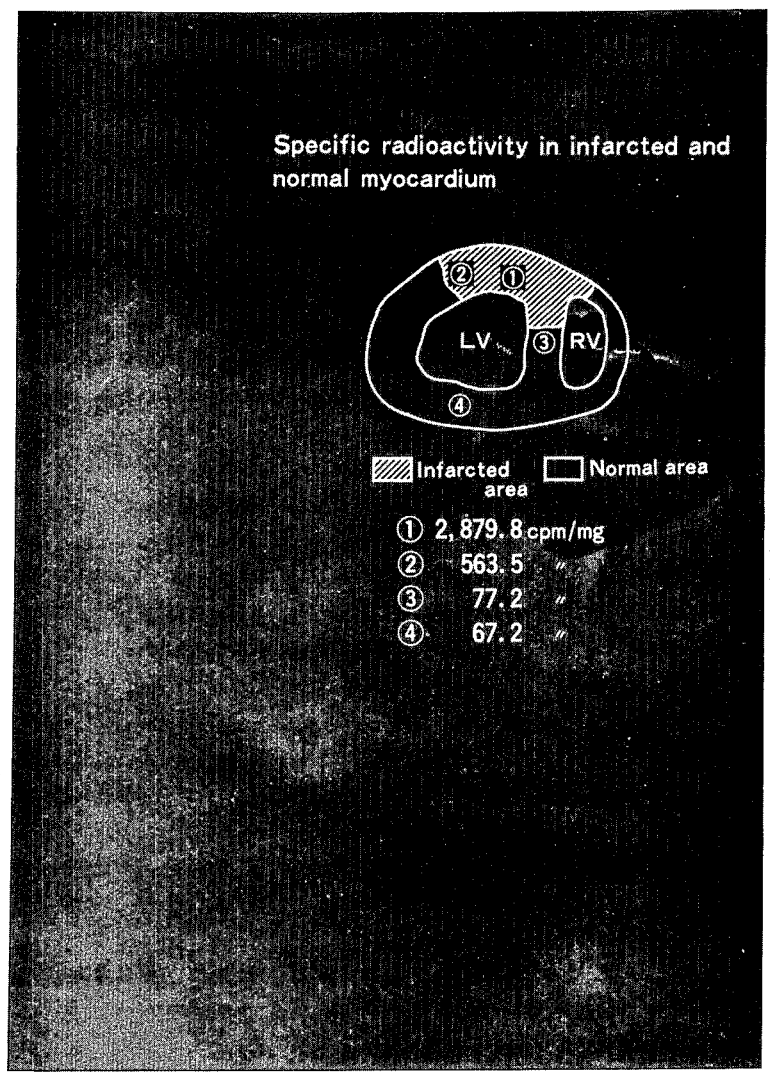

In myocardial infarction, cardiac myosin light chains are released into the blood while large molecules such as cardiac myosin heavy chains stay in dead cells. By utilizing an antibody having specificity to cardiac myosin heavy chain as an imaging agent, the problem concerning the consumption of an antibody in the blood on the route to the infarction site can be dissolved, whereby the radioisotope can be accumulated specifically at the infarction site in a high yield. Therefore, it has become possible to obtain a sharp image of the infarction site at a lower dose level. Further, in comparison with the conventional antibodies derived from anti-serum, this antibody has the advantageous feature of less undesirable side effects such as the induction of an allergic reaction and various other biological reactions due to the formation of an immune complex with the cardiac myosin light chain in the blood.

Further, concerning cardiac muscles, the existence of two isozymes, one being α type having a high ATPase activity and the other being β type having a low ATPase activity, has been known, and, generally speaking, in humans, atrial muscles contain primarily α type, while ventricular muscles contain substantially β type. Accordingly, monoclonal antibodies specific for an isozyme of cardiac myosin heavy chain have the advantageous feature, in addition to those described above, of being usable for localization of myocardial infarction. More specifically, application of monoclonal antibodies having specificity to cardiac myosin heavy chain α type has facilitated the diagnosis of atrial myocardial infarction which has heretofore been extremely difficult. In contrast, application of monoclonal antibodies having specificity to cardiac myosin heavy chain β type makes possible topographic diagnosis of ventricular myocardial infarction by imaging.

These monoclonal antibodies can be supplied stably in great quantities by known methods as useful and highly specific antibodies.

The diagnostic agent of the present invention is obtained by labeling with radioisotopes monoclonal antibodies having specificity to human cardiac myosin heavy chain or human cardiac myosin heavy chain α type or β type (hereinafter, where necessary, referred to generically as "monoclonal antibodies") or the active fragments thereof. These monoclonal antibodies or the active fragments thereof are not particularly limited in preparation method and procedure for labeling with radioisotopes, nor is the diagnostic agent of the present invention limited in form of preparation, which can be suitably selected according to the purpose.

The monoclonal antibody and its active fragment used in the present invention can be prepared respectively by applying the generally practiced cell fusion method (cf. G. Kohler, C. Milstein, Eur. J. Immunol. 6 511-519 (1976) and M. Shulman et al., Nature 276 269-270 (1978)) to obtain a hybridoma producing the antibody and deriving a monoclonal antibody from the hybridoma and by subjecting the monoclonal antibody thus derived to hydrolysis to obtain its active fragment. These procedures will be generally described as follows. (1) Preparation of antibody-producing cells Preparation of antibody-producing cells is carried out by immunizing an xenogenic animal such as mouse, rat, rabbit, sheep, horse, bovine, etc., with a human cardiac myosin heavy chain, human atrial myosin (α type), human ventricular myosin (β type) or a cardiac myosin equivalent immunochemically to the human cardiac myosin heavy chain or human cardiac myosin α type or β type prepared from bovine, horse or hog, and taking antibodyproducing cells from spleen cells, thymocytes, lymphnode cells and/or peripheral blood lymphocytes.

(2) Preparation of myeloma cells

As myeloma cells, cell lines originated from various animals such as mice, rats, rabbits, and humans, can be used. The cell line to be used should preferably be drug resistant, not viable in a selective medium but viable after fusion. The cell line most commonly used is a 8-azaguanine resistant cell line, which is defective in hypoxanthine phosphoribosyl transferase and cannot be grown in hypoxanthineaminopterine-thymidine (HAT) medium. The cell line is also preferably of the "non secretor" type. Typical examples of such cell lines are P3/x63-Ag 8(Nature 256, 495–497 (1975)), P3/x63-Ag 8 U1(P3U1) (ATCC CRL-1597) (Current Topics in Microbiology and Immunology, 81, 1–7 (1978)), P3/x63-Ag 8·6·5·3 (x63·6·5·3) (ATCC CRL-1580) (J. Immunology, 123, 1548–1550 (1979)), P3/NSI-1-Ag 4 - 1 (NS-1) (European J. Immunology, 6, 292–295(1976)), Sp210–Ag 14 (SP2) (ATCC CRL-1581) (Nature, 276, 269–270 (1978)) derived from mouse myeloma MOPC-21 cell line. Rat myeloma 210 RCY 3 Ag 1·2·3 (Y3 Ag 1·2·3) (Nature 277, 131–133 (1979)), and human myeloma U-266-AR$_1$ (Proc. Natl. Acad. Sci. U.S.A., 77, 1158 (1980)), and GM 1500 (Nature, 228, 448 (1980)) are also available. Some of the cell lines listed above are commercially available.

(3) Cell fusion

Cell fusion is carried out by mixing $10^7$ to $10^8$ myeloma cells with antibody producing cells at a mixing ratio of from 1:4 to 1:10 in a medium for culturing animal cells such as Eagle's minimum essential medium (MEM) and RPMI 1640. As a fusing aid, a polyethylene glycol (PEG) having an average molecular weight of 1,000 to 6,000, a polyvinyl alcohol, a virus, or the like is used.

(4) Selection of hybridoma in selective medium

Selection of hybridoma from the cells after cell fusion process is conducted by selective growth in a selective medium. For example, the cells are diluted appropriately with, for example, RPMI 1640 medium containing 15% fetal calf serum, placed on a microtiter plate to about $10^5$–$10^6$ cells/well, and a selective medium (e.g., HAT medium) is added to each well, which step is followed by appropriate exchange of the selective medium. For example, when an 8-azaguanine resistant cell line is used as the myeloma cell and a HAT medium as the selective medium, unfused myeloma cells will die on about the 10th day after cultivation, and the antibody producing cells which are normal cells cannot be grown in vitro for a long term. Accordingly, the cells grown on the 10th to 14th day are all hybridomas.

(5) Screening for antibody producing hybridomas

A screening for hybridomas producing anti-cardiac myosin heavy chain antibody, anti-cardiac myosin heavy chain α antibody or anti-cardiac myosin heavy chain β antibody can be carried out according to the Enzyme Linked Immunosorbent Assay, which will be hereinafter called "ELISA".

More specifically: a cardiac myosin heavy chain α type such as bovine atrial myosin or a cardiac myosin heavy chain β type such as human ventricular myosin is dissolved previously in a buffer such as phosphate buffered saline (PBS) or sodium hydrogen carbonate (pH 8.0) to 10–100 μg/ml; aliquots each of 50 μl are added to a soft plate (96 wells) such as polyvinyl chloride (PVC) plate for ELISA; and the plate is left to stand at 4° C. overnight. Then, the antigen is discarded, and, after washing with PBS, PBS containing 1% bovine serum albumin (BSA) is added. The mixture is then left to stand at room temperature for one hour to block with BSA the sites to which no antigen is bound. Aliquots of 50 μl from the supernatant of each well are added, left to stand at room temperature for one hour, and washed three times with PBS. Then, biotinyl anti-mouse immunoglobulin antiserum (second antibody) is added, and the mixture is left to stand at room temperature for one hour. After washing three times with PBS, avidin D- enzyme complex is added, and the mixture is left to stand at room temperature for 15 minutes. After washing four times with PBS, the optical density is measured with addition of the substrate for the enzyme.

The well which contains a monoclonal antibody specific for the antigen can be easily judged according to the procedure as described above, whereby screening for hybridoma can be carried out.

(6) Cloning

There is the possibility that two or more species of hybridomas are contained in each well, and therefore cloning is conducted according to, for example, the limiting dilution method to obtain a monoclonal antibody-producing hybridoma.

(7) Production of antibody

The most pure monoclonal antibody can be obtained by culturing the hybridoma producing that monoclonal antibody in a medium for culturing animal cells such as RPMI 1640 medium containing 10 to 15% fetal calf serum or serum free medium and obtaining the antibody from the supernatant. For the cell culturing method and conditions, those conventionally used in animal cell culturing method may be suitably applied.

On the other hand, as a method to produce antibodies in a larger amount, it is possible to employ a method in which, after a mineral oil such as pristan (2,6,10,14-tetramethylpentadecane) has been administered intraperitoneally into syngeneic animals from which the parental myeloma of hybridoma has originated, the hybridoma is injected intraperitoneally to be proliferated in a large amount therein. Hybridomas will grow as ascitic tumors within 10-18 days to produce antibodies in high concentrations (about 1 to 20 mg/ml) in serum and ascitic fluid. When purification is required, purification can be carried out after ammonium sulfate fractionation by a method such as DEAE cellulose ion exchange column chromatography, affinity column chromatography using Sepharose 4B having cardiac myosin bound thereto or the like, or gel filtration column chromatography.

(8) Preparation of active fragments

As active fragments, any of (Fab')$_2$ fragment, (Fab') fragment, Fab fragment, and like fragments that retain the immunological properties of the monoclonal antibody used in the present invention can be employed. These active fragments may be prepared from purified monoclonal antibodies in accordance with known procedures such as treatments with papain, pepsine and trypsin. (c.f. "Medicochemical Experiment Method Series Vol. 4 Immunochemistry", Kabushiki Kaisha Nakayama Shoten (August 20, 1972), pp 91–119, "Methods in Immunology and Immunochemistry Vol. 1", pp 422–423, Academic Press, 1967)

The monoclonal antibodies and the fragments thereof thus prepared can also be labeled with radioisotopes by various known methods.

Examples of nuclides of radioisotopes are iodine-125, iodine-123, iodine-131, indium-111, technetium-99m, gallium-67, lead-203, ruthenium-97, mercury-197, thallium-201, and bismuth-212. A method of labeling with these radioisotopes can be selected according to the species thereof. With respect to radioactive iodine, for instance, the chloramine T method, the iodine chloride method or the lactoperoxidase method may be employed. (cf. "Radioisotope Drug Metabolism Experimental Method", Maruzen K. K. (Jan. 30, 1981), pp 95–101, "Methods in Enzymology Vol. 70 Immunochemical Techniques Part A", pp 210–265, Academic Press, 1980) With respect to other radioisotopes, a method in which an antibody or its active fragment is covalently bound to a bifunctional chelating agent, and the product thus obtained is labeled with a radioisotope is applied.

Examples of typical bifunctional chelating agents are 1-amino-6,17-dihydroxy-7,10,28,21-tetraoxo-27-(N-acetylhydroxyimino)-6,11,17,22-tetraazaheptaeicosane (desferrioxamine), 8-hydroxyquinoline, ethylenediaminetetraacetic acid, diethylenetriaminepentaacetic acid (DTPA), diaminocyclohexyltetraacetic acid, 3-aminomethylene-2,4-pentanedionebis (thiosemicarbazone) and the N-alkyl or N-phenyl derivatives thereof, acetylacetone, and citric acid. Coupling of an antibody or its active fragment with a bifunctional chelating agent may be carried out in accordance with a conventional method such as the carbodiimido method, the acid anhydride method or the glutaraldehyde method.

Particularly preferred bifunctional chelating agents are desferrioxamine and dithiosemicarbazone derivatives for technetium-99m and gallium-67 labeling while DTPA is preferred for indium-111 and bismuth-212 labeling. When technetium-99m is used for labeling, a pertechnetiumate is contacted with a reducing agent (e.g., stannous chloride, stannous iodide, or stannous fluoride) to reduce technetium to a tri-, tetra- or pentoxide thereof.

The diagnostic agent of the present invention further encompasses as one embodiment thereof a "kit" comprising a coupled compound of an antibody or its fragment with a bifunctional chelating agent and a radioisotope solution. This kit may be provided with a column for chromatography for purifying the nuclide.

The diagnostic agent of the present invention is administered intravenously into a human body. This diagnostic agent is provided in a form suitable for administration by injection, and may be prepared, for example, by using a solution of sodium chloride or glucose as a carrier. The dose, although varying with the particular radionuclide used for labeling, is ordinarily in the range of from 100 μCi to 30 mCi, preferably from 500 μCi to 3 mCi.

From 1 to 48 hours after administration of the diagnostic agent of the present invention, the patient's heart region is scanned with a scintillation scanner or camera to detect radioactivity originated from the diagnostic agent to obtain an image, whereby diagnosis by imaging will be possible.

Hereinafter, the present invention will be described in more detail with reference to a Reference Example illustrating the preparation of the monoclonal antibodies used in the invention together with Examples, Practice Example and Experimental Example of the diagnostic agent of the invention, it being understood that these examples are presented as illustrative only and not intended to limit the scope of the invention.

REFERENCE EXAMPLE

I. Obtaining hybridoma

Bovine atrial myosin (1 mg/ml) or human ventricular myosin (1 mg/ml) was dissolved in a physiological sodium chloride solution and mixed with complete Freund's adjuvant in a ratio of 1:1 to prepare an emulsion. The emulsion was administered intraperitoneally into a BALB/C mouse (female, 6 weeks old) several times every two weeks (50 μg/head), and finally 30 μg of bovine atrial myosin or human ventricular myosin was administered intravenously.

Three days after the final immunization, spleen cells were taken out of the mouse and washed with MEM. Mouse myeloma $P_3U_1$ was washed with MEM and mixed with the spleen cells in a ratio of 10:1. After centrifugation, 1 ml of 50% PEG 1000 MEM solution was gradually added to a pellet or cake thus obtained to carry out cell fusion. Further, the MEM solution was gradually added to obtain a final quantity of 10 ml. Again, centrifugation was conducted, and the pellet was suspended in RPMI 1640 medium containing 15% fetal calf serum to $1 \times 10^5$ cells/0.1 ml as $P_3U_1$ and plating on a 96-well microplate in 0.1 ml/well.

One day later, aliquots each of 0.1 ml of HAT medium were added, and, thereafter every 3–4 days, half of the medium was renewed with fresh HAT medium. On about the 7th day, growth of hybridoma was recognized in some of the wells.

0.05 ml of the supernatant where hybridoma was grown were added to a 96-well microplate previously coated with bovine atrial myosin (α type) or human ventricular myosin (β type). By using avidin D-peroxidase (produced by Vector Co.) as the avidin D-enzyme conjugate, and hydrogen peroxide, 4-aminoantipyrine and phenol as the substrate and the chromogenic agent, according to the ELISA method as described above, the supernatant containing a monoclonal antibody for cardiac myosin heavy chain which reacts with both atrial and ventricular myosins, the supernatant which reacts with bovine atrial myosin but does not react with human ventricular myosin (monoclonal antibody having specificity to cardiac myosin heavy chain α type is contained in this supernatant), and the supernatant which reacts with human ventricular myosin but does not react with bovine atrial myosin (monoclonal antibody having specificity to cardiac myosin heavy chain β type is contained in this supernatant) were selected and the hybridomas were cloned by limiting dilution As a result, hybridomas CMA-25 cell line and CMA-34 cell line producing an antibody having specificity to cardiac myosin heavy chain; CMA-19 cell line producing an antibody having specificity to cardiac myosin heavy chain α type; and HMC-14 cell line, HMC-48 cell line and HMC-50 cell line producing an antibody having specificity to cardiac myosin heavy chain β type were obtained.

II. Production of monoclonal antibody

Each of the hybridomas listed above was cultured in an RPMI 1640 medium containing 15% fetal calf serum in a 96-well microplate, then with scale-up to 25 cm² flask and 75 cm² flask, and the culture supernatants were collected.

Titers of the monoclonal antibodies in these supernatants were determined by the ELISA method. The titer is expressed as dilution magnitude of the antibody sample from the original solution which gives 50% of the absorbance, taken as 100%, which is obtained by the ELISA method for the sample in which a sufficient amount of antibody exists relative to the coated antigen.

Further, the subclass of each of the antibodies was determined by means of a MONOABID EIA KIT (supplied by ZYMED Co.).

The results obtained are summarized in Table 1.

TABLE 1

| Hybridoma cell line | Titer with respect to bovine atrial myosin | Titer with respect to human ventricular myosin | Titer with respect to human ventricular myosin light chain | Subclass |
|---|---|---|---|---|
| CMA-25 | 25 | 125 | — | $IgG_1/\kappa$ |
| CMA-34 | 25 | 625 | — | $IgG_{2b}/\kappa$ |
| CMA-19 | 25 | — | — | $IgG_1/\kappa$ |
| HMC-14 | — | 125 | — | $IgG_{2a}/\kappa$ |
| HMC-48 | — | 625 | — | $IgG_{2b}/\kappa$ |
| HMC-50 | — | 625 | — | $IgG_{2b}/\kappa$ |

EXAMPLE 1

(production of $^{131}$I-labeled anti-human ventricular myosin heavy chain β type monoclonal antibody)

$5 \times 10^6$ cells/head of hybridoma HMC-48 cell line were administered into mice which had been previously administered with pristan to induce ascitic tumors. The ascitic fluids obtained from the mice 10 to 20 days after administration were pooled to obtain a 50% saturated ammonium sulfate fraction. This fraction was then subjected to DE52 column chromatography to elute therefrom a purified monoclonal antibody (HMC-48).

To 3 mCi of $^{131}$I were added 200 μl of the purified antibody (8.7 mg/ml) thus obtained, 150 μl of chloramine T (1 mg/ml), 600 μl of sodium metabisulfite (1 mg/ml), 150 μl of potassium iodide (50 mg/ml), and 150 μl of a 0.5 M phosphate buffer (pH 7.5). The mixture, after being reacted for one minute at room temperature, was subjected to column chromatography by using Sephadex G-50 equilibrated previously with a 0.5% bovine serum albumin-phosphate buffer to separate free $^{131}$I to obtain a $^{131}$I-monoclonal antibody (HMC-48).

EXAMPLE 2

(Production of $^{111}$In-labeled anti-human ventricular myosin heavy chain β type monoclonal antibody (Fab')₂ fragment)

26 mg of the purified monoclonal antibody (HMC-48) produced in Example 1 were dialyzed against a sodium acetate-hydrochloride buffer (pH 4.5), and 2.6 ml of an antibody solution (10 mg/ml) was formed with the buffer. To this solution was added 0.5 mg of pepsine (2948 U/mg, supplied by Millipore Co.), and the mixture was caused to react for 18 hours at 37° C.

After reaction, the mixture was dialyzed against 1 liter of a borate buffer (pH 8.0), the buffer being renewed twice during the dialysis Subsequently, the mixture was subjected to gel filtration column chromatography using Ultrogel AcA 34 (supplied by Bio-Rad Co.) equilibrated with 50 mM phosphate buffer, and fractions having a molecular weight peak of around 100,000 were collected as (Fab')₂ fragments.

The fragment thus obtained was concentrated to 5 mg/ml through Amicon B-15; the concentrate gradually mixed with a carboxycarbonic acid anhydride mixture of diethylenetriaminepentaacetic acid (DTPA) by the Krejcarek et al. method (Biochem. Biophys. Res. Commun., Vol. 77, pp.581–587 (1977)); and the mixture was caused to react overnight at 4° C.

The reaction solution was then dialyzed against 0.1 M acetate buffer (pH 5.0), and (Fab')₂-DTPA fractions were collected through Sephadex G-25, which fractions were dialyzed against 0.1M glycine-hydrochloride buffer (pH 3.5). The HMC-48 (Fab')$_2$-DTPA thus obtained was mixed with indium chloride $^{111}$In the buffer, and the mixture was caused to react for 30 minutes. As a result, 1.5 mCi/mg protein of HMC-48(Fab')$_2$-DTPA-$^{111}$In was obtained.

EXAMPLE 3

(Production of $^{111}$In-labeled anti-human cardiac myosin heavy chain monoclonal antibody (Fab')$_2$ fragment)

A monoclonal antibody (CMA-34) was treated similarly as in Example 2 to obtain a (Fab')$_2$ fragment.

To the fragment obtained was then bound DTPA by the procedure of Example 2 and reacted with $^{111}$In. As a result, CMA-34(Fab')$_2$-DTPA-$^{111}$In having a specific radio activity of 1.1 mCi/mg protein was obtained.

EXAMPLE 4

(Production of lllIn-labeled anti-human atrial myosin heavy chain $\alpha$ monoclonal antibody Fab fragment)

A monoclonal antibody (CMA-19) was purified similarly as in Example 1 and freeze-dried.

30 mg of the antibody thus purified was added to 2.5 ml of a phosphate buffer (pH 7.0), and to the mixture obtained was added 0.3 mg of pepsine (supplied by Sigma Co.). The resultant mixture was caused to react for 2 hours at 37° C.

The reaction solution was subjected to affinity column chromatography using a column packed with Protein A Sepharose CL-4B (supplied by Pharmacia Fine Chemicals) equilibrated previously with a phosphate buffer (pH 7.4) for adsorption of Fc fragments and unfragmented antibodies. Unadsorbed fractions were collected and concentrated to 5 mg/ml through Amicon B-15. To the Fab fragment thus obtained was bound DTPA by the procedure of Example 2 to produce CMA-19Fab-DTPA-$^{111}$In having a specific radioactivity of 1.3 mCi/mg protein.

EXAMPLE 5

(Production of $^{111}$In-labeled anti-human ventricular myosin heavy chain $\beta$ type monoclonal antibody Fab fragment)

To ascitic fluid induced by hybridoma HMC-48 cell line similarly as in Example 1 were added an equal volume of phosphate buffered saline (PBS) (pH 7.0) and a two-fold volume of saturated ammonium sulfate. A precipitate thus formed was centrifuged off, and then the ascitic fluid was fractionated with 50% saturated ammonium sulfate. The resulting precipitate was dialyzed against 0.1 M Tris-hydrochloride buffer (pH 7.2) and subjected to DE52 column chromatography with use of 0.1 M Tris-hydrochloride buffer (pH 7.2). The pass-through fraction was concentrated and subjected to Ultrogel AcA 44 (supplied by LKB Co.) column chromatography using PBS to obtain an immunoglobulin fraction having a molecular weight of 150,000 as a purified antibody.

To a solution (30 mM PBS plus 5 mM EDTA) of the purified antibody (5 mg/ml) was added an equal volume of a 0.025% papain solution (supplied by Cooper Biochemical Co., 30 mM PBS (pH 7.0), 5 mM cysteine plus 2 mM EDTA), and the mixture was caused to react for 30 minutes at 37° C. At this stage, 10 mM iodoacetamide solution was added to the mixture to terminate the reaction.

The reaction solution was applied to Protein A-Sepharose CL-4B column equilibrated with 0.1 M Tri-shydrochloride buffer (pH 8.0). The pass-through fraction was concentrated, and was further applied to Ultrogel AcA 54 (supplied by LKB Co.) column equilibrated with PBS (pH 7.0) to obtain a Fab fragment having a molecular weight of 50,000.

To the Fab fragment obtained in the manner described above was bound DTPA by the procedure of Example 2, and the HMC-48Fab-DTPA thus obtained was mixed with indium chloride $^{111}$In in 0.1 M glycinehydrochloride buffer (pH 3.5). The mixture was caused to react for 30 minutes to obtain 1.5 mCi/mg protein of $^{111}$In-labeled HMC-48Fab-DTPA.

PRACTICE EXAMPLE (Diagnosis with $^{131}$I-monoclonal antibody (HMC-48))

2 mCi of the $^{131}$I-monoclonal antibody (HMC-48) obtained in Example 1 was administered intravenously into a dog with myocardial infarction artificially induced by ligating the coronary artery. 36 hours after administration, a planar image and a single photon emission computed tomography (SPECT) were obtained by a gamma scintillation camera (Maxicamera 400 AT, supplied by General Electric Co.).

In the planar image, the $^{131}$I-monoclonal antibody accumulated at the infarction site in the canine ventricular muscle. This antibody was also found to accumulate slightly in the thyroid gland only, but was not found to accumulate in the bones or anywhere else as opposed to 99mTc-pyrophosphate.

In the computed tomography, on the other hand, the infarction site was clearly depicted, and the $^{131}$I-monoclonal antibody accumulated in the apex and a part of the septum.

EXPERIMENTAL EXAMPLE 1 mg of the $^{111}$In-labeled HMC-48Fab-DTPA (1.5 mCi/mg) obtained in Example 5 was administered intravenously into a dog with myocardial infarction artificially induced by ligating the coronary artery. 48 hours after administration, the heart was excised out of the dog. From the excised heart, specimens each of a size of about 3×3 mm were prepared, and the radioactivity at the infarction site and that at the non-infarction site were respectively measured.

The radioactivity was 2879.8 cpm/mg at the infarction site, 563.5 cpm/mg on the periphery thereof, and 77.2 cpm/mg and 67.2 cpm/mg in the normal regions, about 40-fold radioactivity accumulating at the infarction site in comparison with the normal regions.

What is claimed is:

1. A diagnostic agent for heart disease comprising a radiolabeled monoclonal antibody having specificity to human cardiac myosin heavy chain or its active fragment.

2. A diagnostic agent according to claim 1, in which the radiolabeled monoclonal antibody recognizes an isozyme of human cardiac myosin heavy chain.

3. A diagnostic agent according to claim 1, in which the radiolabeled monoclonal antibody has specificity to human cardiac myosin heavy chain $\alpha$ type.

4. A diagnostic agent according to claim 1, in which the radiolabeled monoclonal antibody has specificity to human cardiac myosin heavy chain $\beta$ type.

5. A method for the diagnosis of heart disease which comprises administering a radiolabeled monoclonal antibody having specificity to human cardiac myosin heavy chain or its active fragment to a subject, and detecting the site at which the human cardiac myosin heavy chain is exposed by measuring the radioactivity originated from the radiolabeled monoclonal antibody or its active fragment.

6. A diagnostic agent according to claim 1 in the form of an aqueous injection suitable for administration into the human body by injection.

7. A kit for use as a diagnostic agent for heart disease comprising a radiolabeled monoclonal antibody having specificity to a human cardiac myosin heavy chain or its active fragment said antibody or its active fragment being in combination with a bifunctional chelating agent and, separately, a radioisotope solution.

8. A kit according to claim 7 in which an active fragment is coupled with the chelating agent.

* * * * *